# United States Patent [19]

Martin

[11] Patent Number: 5,085,351
[45] Date of Patent: Feb. 4, 1992

[54] ADJUSTABLE DOSE DISPENSER

[76] Inventor: James H. Martin, 8322 County Line Rd., Burr Ridge, Ill. 60521

[21] Appl. No.: 608,690

[22] Filed: Nov. 5, 1990

[51] Int. Cl.⁵ .............................................. B65D 83/14
[52] U.S. Cl. .................................... 222/287; 222/288; 222/402.2; 222/434
[58] Field of Search ................ 222/282, 287, 288, 309, 222/394, 402.1, 402.17, 402.2, 434, 435, 438

[56] References Cited

U.S. PATENT DOCUMENTS

| | | | |
|---|---|---|---|
| 3,055,560 | 9/1962 | Meshberg | 222/434 X |
| 3,104,785 | 9/1963 | Beard, Jr. | 222/402.2 X |
| 3,180,535 | 4/1965 | Ward | 222/309 X |
| 3,211,346 | 10/1965 | Meshberg | 222/309 X |
| 3,221,946 | 12/1965 | Riley | 222/309 |
| 4,427,137 | 1/1984 | Dubini | 222/288 X |
| 4,858,790 | 8/1989 | Howlett | 222/402.2 |
| 4,892,232 | 1/1990 | Martin | 222/402.2 X |

FOREIGN PATENT DOCUMENTS 2605474 8/1976 Fed. Rep. of Germany ... 222/402.2

Primary Examiner—Kevin P. Shaver

[57] ABSTRACT

A liquid dispensed in adjustable, predetermined quantities from a pressurized reservoir upon each actuation of a metering and dispensing valve incorporated in the dispenser. A flexible sleeve is disposed between the reservoir chamber and a selected one of a plurality of differently sized metering chambers to expel the contents of the selected metering chamber when the metering and dispensing valve is actuated. The metering chambers are carried by a rotatably adjustable member which is mounted to the stem of the metering and dispensing valve.

9 Claims, 3 Drawing Sheets

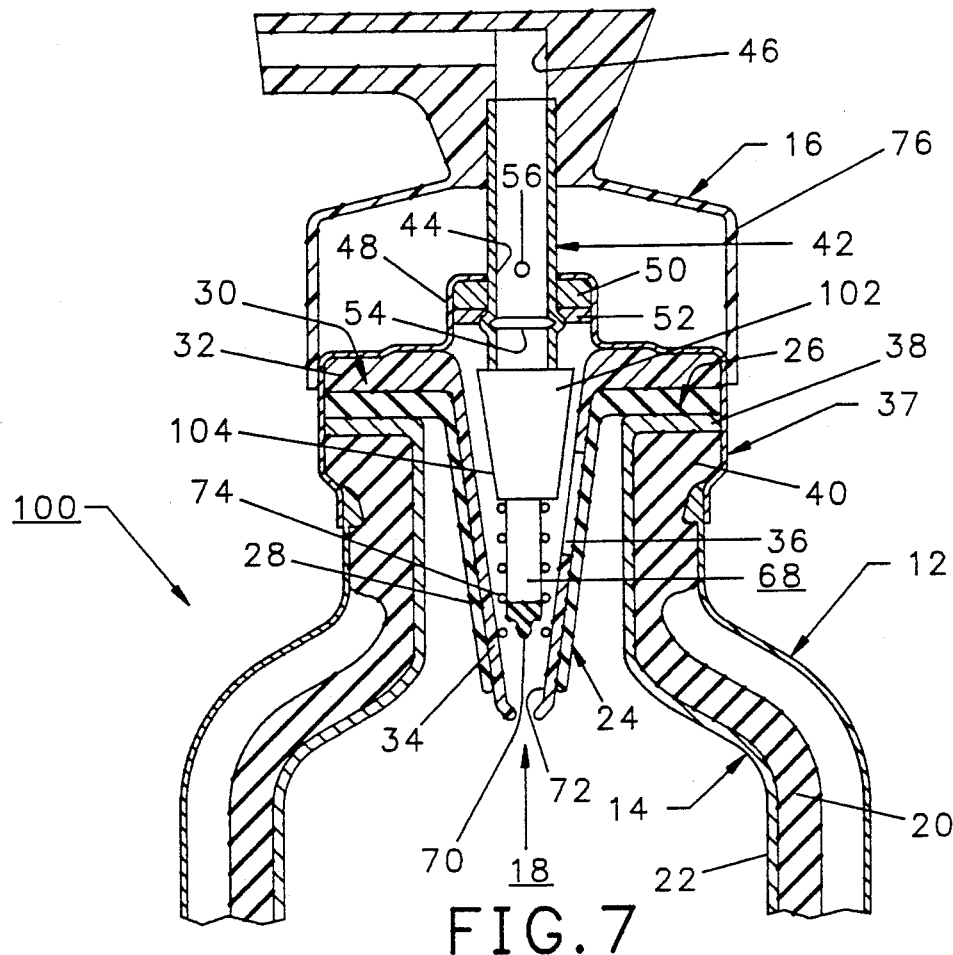
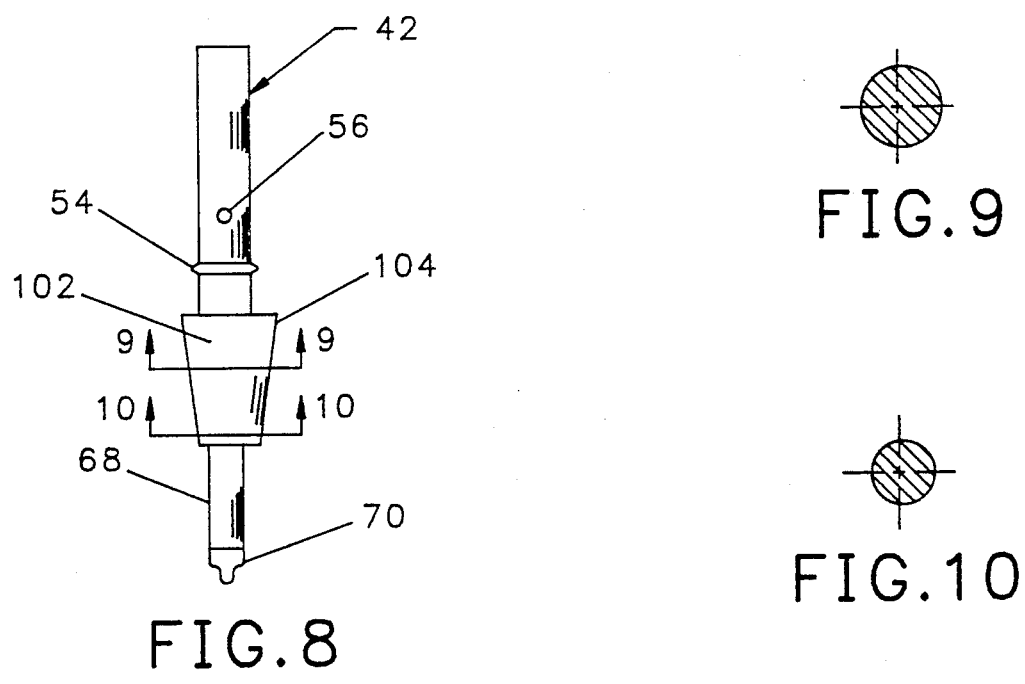

ADJUSTABLE DOSE DISPENSER

The present invention relates in general to a pressurized, unit dose liquid dispenser, and it relates in particular to a new and improved pressurized liquid dispenser which emits an adjustable, premeasured dose of liquid each time the dispenser is actuated.

BACKGROUND OF THE INVENTION

Devices for dispensing predetermined quantities of a pressurized liquid are described in U.S. Pat. Nos. 3,104,785 and 4,892,232. For some applications, such as in the administration of insulin, it would be desirable to permit adjustment of the dose which is dispensed upon each actuation of the dispenser.

Recently it has been found that insulin can be advantageously administered in the form of a spray applied to the nasal tissues of the patient. Since the prescribed doses of insulin vary over a relatively wide range, it is not possible to use any single unit dispenser for all patients unless each actuation of the dispenser emits only a very small quantity of insulin constituting a small percentage of a prescribed dose, thereby necessitating repeated operation of the dispenser for each prescribed dose of insulin. This multiple operation of the dispenser for each dose requires that the patient accurately count the number of times the dispenser is actuated to insure that the prescribed dose is administered. This procedure is not only unecessarily time consuming, but it can result in the improper administration of medication to the patient.

Therefor, it would be desirable to provide a dispenser which emits an adjustable, but precise, dose of insulin or other liquid upon each actuation of the dispenser. Preferably, the adjustment should be made without the use of special tools or the like so as to permit the physician as well as the patient to easily adjust the dose to be dispensed upon each actuation of the dispenser.

SUMMARY OF THE INVENTION

Briefly, there is provided in accordance with one aspect of the present invention a novel liquid dispenser which emits an adjustable dose of liquid upon each actuation of the dispenser. The dispenser includes a reservoir containing a pressurized supply of the liquid to be dispensed, a metering chamber having an adjustable volume which is automatically filled with the liquid from the reservoir while the dispenser is in the inoperative condition, and a dispensing orifice which communicates with the metering chamber when a metering and dispensing valve is actuated to dispense the contents of the metering chamber to the patient.

In one embodiment of the invention a plurality of metering chambers of different volumetric capacity are provided, and these chambers are adapted to be selectively moved from an inoperative to an operative position so that only the amount of liquid in the selected metering chamber is dispensed when the valve is actuated. In the preferred embodiment of the invention, the metering chambers are mounted on the stem of the metering and dispensing valve and are arranged about the periphery of the valve stem so as to be selectively brought into the operative position opposite an elastomeric discharge member interposed between the reservoir and the selected metering chamber by rotation of the valve stem. The valve stem is accessible from the outside of the dispenser so as to facilitate adjustable rotation thereof.

GENERAL DESCRIPTION OF THE DRAWINGS

Further objects and advantages and a better understanding of the present invention may be had by reference to the following detailed description taken in connection with the accompanying drawings wherein:

FIG. 7 is a fragmentary elevational view, partly in cross-section of another embodiment of the present invention which provides an infinitely adjustable unit dose dispenser;

FIG. 8 is an isometric view of one element of the dispenser shown in FIG. 7;

FIG. 9 is a cross-sectional view taken along the line 9—9 of FIG. 8; and

FIG. 10 is a cross sectional view taken along the line 10—10 of FIG. 8.

DETAILED DESCRIPTION OF A PREFERRED EMBODIMENT

Figure 1:
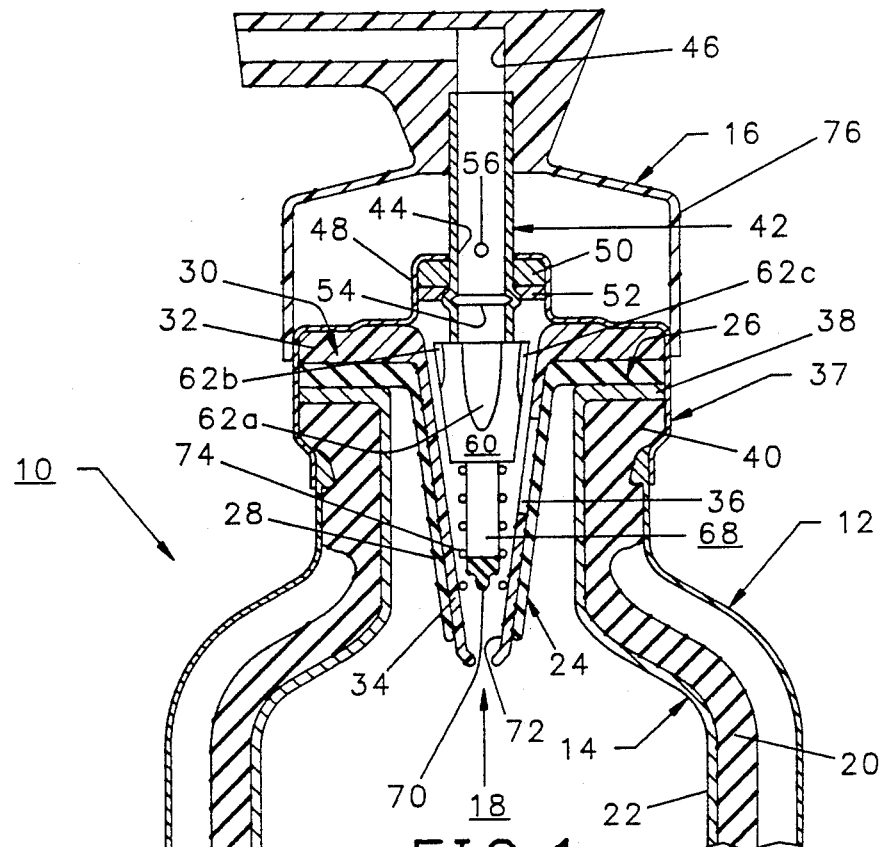
FIG. 1 is a fragmentary, elevational view, partly in cross-section, showing the metering and dispensing valve of a unit dose dispenser embodying the present invention, the dispenser being shown in the inoperative fill position.
Figure 2:
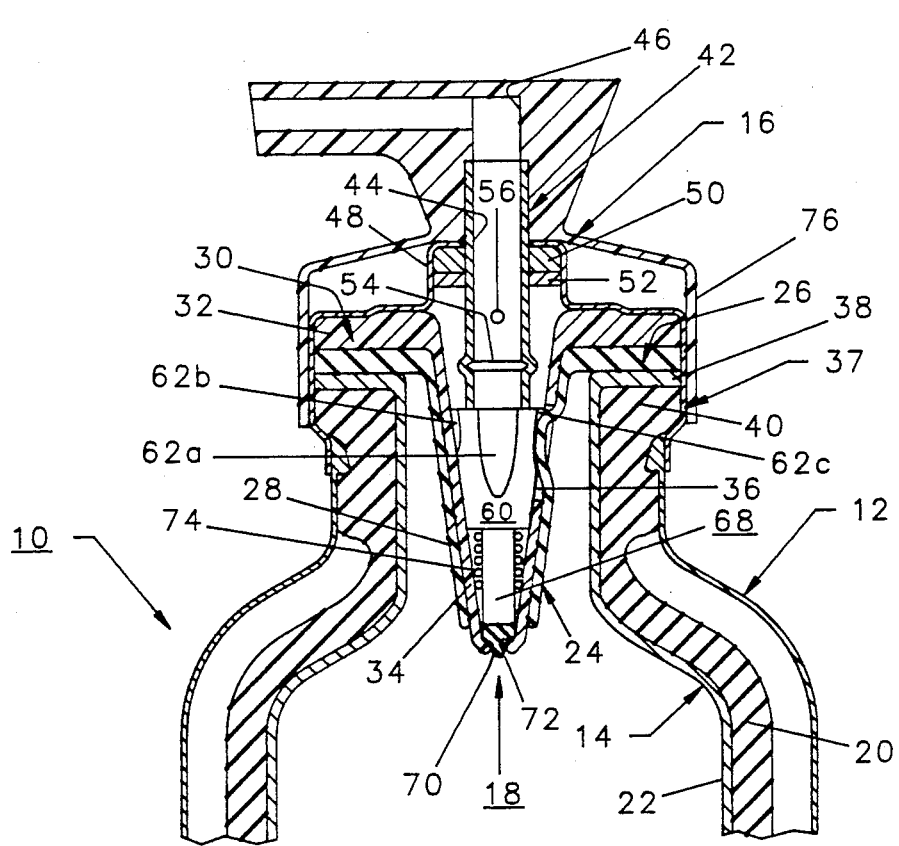
FIG. 2 is a fragmentary, elevational view, partly in cross-section, of the dispenser of FIG. 1, the dispenser being shown in the operative dispensing position.
Figure 3:
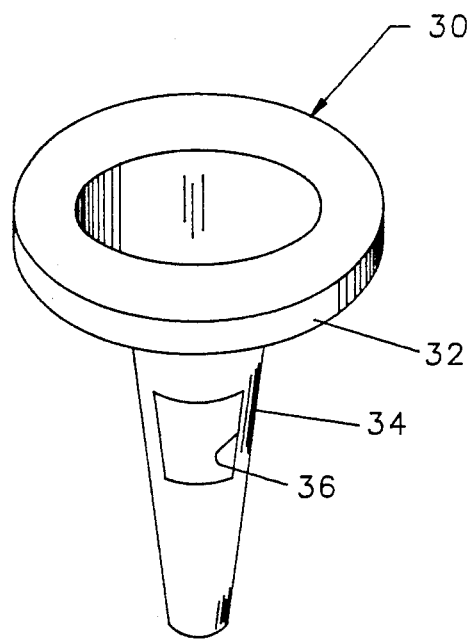
FIG. 3 is an isometric view of an element of the dispensing valve of the dispenser of FIG. 1.

Referring particularly to FIGS. 1 and 2, a unit dose liquid spray dispenser 10 may be seen to include as its principal elements a rigid outer shell 12 formed of a suitable protective material such as metal, glass or plastic, an elastomeric reservoir 14 disposed entirely within the shell 12, a combined dispensing nozzle and dispenser actuator 16, and a dispensing valve assembly identified generally by the reference number 18. A liquid to be dispensed in prescribed doses fills the chamber within the reservoir 14 and is maintained under pressure by an elastomeric sleeve 20 which had been stretched during the supply of the liquid under pressure to a closed flexible plastic container 22 positioned within the sleeve 20. A pressurized reservoir of this general type is described in U.S. Pat. No. 4,387,833. It will be understood by those skilled in the art, however, that other types of pressurized reservoirs, such as the aerosol type, may be used for some applications in place of a pressurized elastomeric reservoir.

The dispensing valve assembly 18 includes a generally tubular flexible member 24 having an annular mounting and sealing flange 26 at the top and a centrally disposed generally conical portion 28 which depends into the reservoir. Mounted above and within the member 24 is a generally tubular, rigid member 30 having an annular, external flange 32 at the top and a central conical portion 34 which fits tightly within the conical portion 28 of the member 24. A trapezoidal shaped window 36 is provided in the conical portion 34 of the member 30 near the bottom thereof and as shown in FIGS. 1 and 2 is covered by the flexible member 24.

The parts 12, 14, 20, 24 and 30 are held together in mutually assembled relationship by means of a metallic locking cap 37 which fits over external flanges on the respective parts as shown in FIGS. 1 and 2. An annular flange 38 at the top of the container member 22 is sealingly compressed between an annular flange 40 at the top of the elastomeric sleeve 20 and the annular flange 26 at the top of the member 24.

A tubular valve stem 42 extends upwardly through a central opening 44 in the cap 37 into a bore 46 in the nozzle and actuator member 16. The cap 37 is provided with an inverted cup-like central section 48 in which a pair of sealing washers 50 and 52 are positioned in superimposed relationship in sealing engagement with the external surface of the valve stem 42. An external annular ridge 54 is provided on the valve stem 42 and provides a stop surface which abuts the bottom surface of the lower sealing washer 52 to prevent spurious withdrawal of the valve stem from the dispenser. An orifice 56 is provided in the wall of the valve stem 42 at a location so as to be sealably closed by the upper sealing washer 50 when the dispenser is in the inoperative position shown in FIG. 1. As is described in greater detail hereinafter, when the valve stem is depressed to dispense a dose of liquid through the nozzle, the liquid dose is conducted through the orifice 56 to the nozzle.

Figure 5:
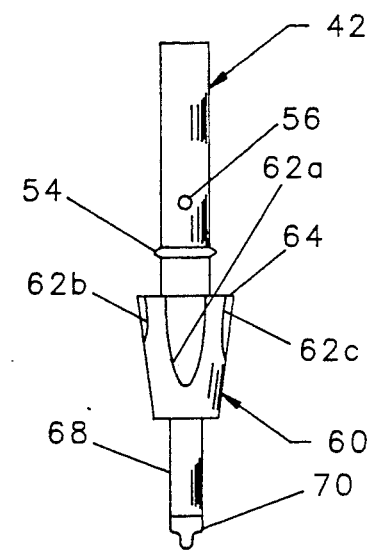
FIG. 5 is an isometric view of the stem and metering chambers used in the dispenser of FIG. 1.
Figure 4:
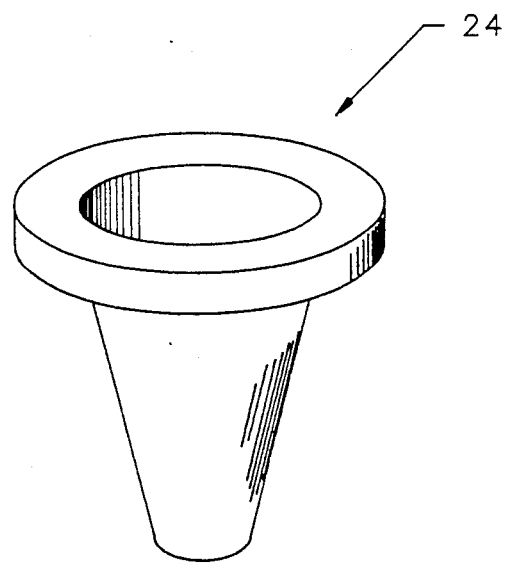
FIG. 4 is an isometric view of a resilient dispensing member used in the dispenser of FIG. 1.

With further reference to FIG. 5, a frustoconical metering chamber carrying member 60 is fixedly mounted on the valve stem 42 below the ridge 54 in coaxial relationship therewith. The external profile of the member 60 is complementary to the portion of the member 30 containing the window 36 and is provided with a plurality of parabolic recesses 62a, 62b, and 62c which open onto the top surface 64 of the member 60. The recesses are of different sizes and provide metering chambers of a plurality of different sizes. In the disclosed embodiment, there are four such recesses, only three of which are visible in the drawing. When the nozzle and actuator 16 is fully depressed, the member 60 fits tightly against the inner surface of the member 30 with one of the recesses 62 directly opposite the window 36. The pressure in the reservoir forces the portion of the member 24 disposed opposite the window 36 through the window against the surface of the respective recess to expel the volume of the recess through the stem and the orifice 56 to the dispensing nozzle. It will thus be seen that the volume of the recess disposed opposite the window 36 determines the quantity of liquid which is dispensed each time the nozzle and actuator 16 is depressed.

A rod 68 depends from the member 60 in coaxial relationship with the valve stem 42, and a resilient valve member 70 is mounted to the bottom end thereof. The lower end of the member 30 is inturned to provide a lip 72 which functions as an annular valve seat 72 against which the valve member 70 is compressed when the nozzle and actuator member 16 is fully depressed. A coil spring 74 surrounds the rod 68 and is held in compression between the lip 72 and the bottom of the member 60 to bias the valve to the inoperative position.

When the valve is in the inoperative position shown in FIG. 1, the chamber within the member 30 is in direct communication with the reservoir chamber, and liquid is thus transfered thereto filling all of the metering recesses as well as the remainder of the chamber. When the nozzle and actuator member 16 is subsequently depressed to the position shown in FIG. 2, the valve member 70 is sealably seated against the seat 72 to seal the metering chambers from the reservoir. At this same time, the orifice 56 in the valve stem is located below the sealing washers 50 and 52 so as to communicate the metering chambers to the nozzle. The pressure in the reservoir forces the flexible member into the particular recess positioned opposite the window 36 to force from the inner chamber in the member 30 an amount of liquid equal to the volume of the particular recess positioned opposite the window 36.

Figure 6:
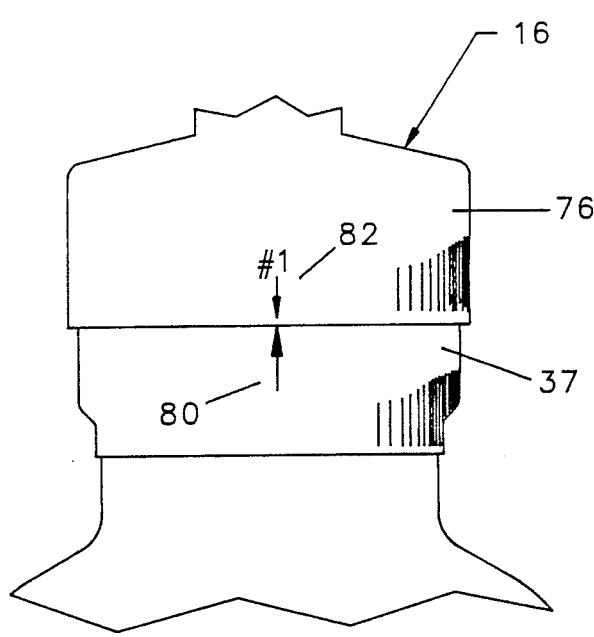
FIG. 6 is a fragmentary elevational view of the nozzle and actuator member, and the upper portion of the container of the dispenser shown in FIG. 1.

In order to adjust the amount or volume dispensed upon each actuation of the nozzle and actuator 16, it is merely necessary to rotate the nozzle and actuator 16 and the valve stem which is affixed thereto to one of a plurality of angular positions wherein the recesses 62 are opposite the window. Suitable indicia are provided on the cap 37 and on a depending flange portion 76 on the nozzle and actuator member 16 to facilitate such selection. As shown in FIG. 6, a reference arrow 80 aligned with the central vertical axis of the window 36 is provided on the cap 37, and four arrows 82 are provided on the flange 76 at the respective locations of the vertical center lines of the metering recesses 62. If desired, a detent, not shown, may be provided between the flange 76 and the cap 37 or in any other suitable location to hold the member 60 in the selected angular position.

Referring to FIGS. 7 and 8, there is illustrated another embodiment of the invention in the form of a dispenser 100 wherein the volume of liquid which is dispensed upon each actuation of the dispenser is infinitely adjustable. Most of the parts of the dispenser 100 are identical to corresponding parts in the dispenser 10 shown in FIGS. 1 and 2, and therefore, similar parts are identified by like reference numbers.

As shown, a chamber volume adjusting member 102 is mounted to the valve stem 42 above the spring 74 and has an eccentric external surface 104 having a configuration which may be best understood by reference to FIGS. 9 and 10. It may be seen that as the stem 42 is rotated the space between the peripheral surface of the member 102 and the window 36 in the member 30 is varied so that when the member 24 is pressed through the window 36 into engagement with the surface 102 the volume of liquid which is dispensed is also varied.

While the present invention has been described in connection with particular embodiments thereof, it will be understood by those skilled in the art that many changes and modifications may be made thereto without departing from the true scope and spirit of the invention. Therefore, it is intended by the appended claims to cover all such changes and modifications which come within the true spirit and scope of the present invention.

I claim:
1. A unit dose dispenser, comprising in combination
a pressurizable reservoir having a first chamber therein for containing a supply of liquid under pressure,
nozzle means for dispensing said liquid from said reservoir,
second chamber means for containing a quantity of said liquid,
dispensing valve means disposed between said second chamber and said nozzle means and including a rotatable tubular valve stem axially movable between a fill position wherein said second chamber is filled with said liquid from said first chamber and a dispensing position wherein a predetermined volume of the liquid from said second chamber is supplied to said nozzle means when said valve stem is axially moved from said fill position to said dispensing position, and means for adjusting said predetermined volume, said means for adjusting said predetermined volume is mounted on said valve stem and is responsive to the angular position of said valve stem to selectively adjust the predetermined volume of said liquid to be dispensed through said valve stem to said nozzle means.

2. A unit dose dispenser according to claim 1, wherein said second chamber has a constant volume when filled with said liquid.

3. A unit dose dispenser according to claim 1 comprising spring means urging said valve stem to said fill position.

4. A dispenser for dispensing an adjustable dose of fluid in response to each actuation of said dispenser, comprising in combination reservoir means for containing a supply of liquid under pressure, a nozzle for dispensing a quantity of said liquid supplied thereto, a plurality of metering chamber recesses mounted within said reservoir means, first valve means connected between said metering chamber recesses and said reservoir for communicating said metering chamber recesses to said reservoir when said valve means is in a first position and for sealing said metering chamber recesses from said reservoir when said valve means is in a second position, second valve means connected between said metering chamber recessses and said nozzle when said second valve means is in a first position and for sealing said metering chamber recessess from said nozzle when said second valve means is in a second position, said first and second valve means being interconnected for simultaneous operation, manually adjustable means for selecting one of said metering chamber recesses, and means for expelling the liquid from the selected one of said metering chamber recesses when said first valve means is in said second position and said second valve means is in said first position.

5. The dispenser according to claim 4, further comprising a valve stem, said first and second valve means being mounted on said valve stem, and a member carrying said metering chamber recesses, said member being mounted on said valve stem.

6. The dispenser according to claim 4, said metering chamber recesses being angularly positioned around said valve stem whereby said metering chambers are individually selectable by rotation of said valve stem.

7. The dispenser according to claim 4, comprising an imperforate flexible member interposed between the one of said metering chamber recesses in the selected position and said reservoir, said flexible member being forced into the selected one of said metering chamber recesses by the pressure in said reservoir when said dispenser is actuated.

8. The dispenser according to claim 6 wherein said member is eccentric with respect to the longitudinal axis of said valve stem.

9. A unit dose dispenser, comprising in combination a container, a nozzle and actuator member mounted to said container, a pressurizable reservoir having a chamber therein for containing a supply of liquid under pressure, dispensing valve means connected between said chamber and said nozzle, means, metering chamber means connected to said valve means for containing a volume of said liquid and for supplying a predetermined volume of said liquid from said metering chamber to said nozzle upon each actuation of said valve means, and means including an eccentric surface for adjusting said predetermined volume, said dispensing valve means comprising a rotatable valve stem axially movable between a fill position wherein said metering chamber means is filled with said liquid and a dispensing position wherein said predetermined volume of liquid is dispensed from said metering chamber means, and said means for adjusting said predetermined volume of liquid is mounted on said valve stem and is responsive to the angular position of said valve stem.

* * * * *